United States Patent [19]

Chiaramonte et al.

[11] Patent Number: 4,568,285

[45] Date of Patent: Feb. 4, 1986

[54] MASTICATION FORCE DAMPENING DENTAL JAWBONE IMPLANT

[76] Inventors: Vincent Chiaramonte, 75 Farmers Ave., Lindenhurst, N.Y. 11757; Richard Bernstein, 4 Dogwood Hill, Brookville, N.Y. 11545; Allen Motola, 10 Chernucka Ave., Merrick, N.Y. 11566

[21] Appl. No.: 689,138

[22] Filed: Jan. 7, 1985

[51] Int. Cl.⁴ ............................................. A61C 8/00
[52] U.S. Cl. ................................... 433/173; 433/169
[58] Field of Search ................. 433/173, 174, 175, 72, 433/169

[56] References Cited

U.S. PATENT DOCUMENTS

| 711,324 | 10/1902 | Lacy | 433/173 |
|---|---|---|---|
| 4,439,152 | 3/1984 | Small | 433/173 |
| 4,488,875 | 12/1984 | Nizick | 433/173 |
| 4,511,336 | 4/1985 | Hidaka et al. | 433/173 |

*Primary Examiner*—Robert Peshock
*Attorney, Agent, or Firm*—James P. Malone

[57] ABSTRACT

Mastication force dampening dental implant has a cylindrical casing adapted to be implanted in a jawbone. A resilient insert is mounted in the casing and has a first shaftway. A nut is anchored in the insert coaxially with the first shaftway. A threaded shaft is mounted in the first shaftway, the shaft being threaded into the nut. The shaft has a second shaftway in its top portion. A head is fixedly connected to the first shaft at the top of the casing. A tooth or denture retention post is mounted on the head. The retention post is removably mounted in the top of the second shaftway.

8 Claims, 6 Drawing Figures

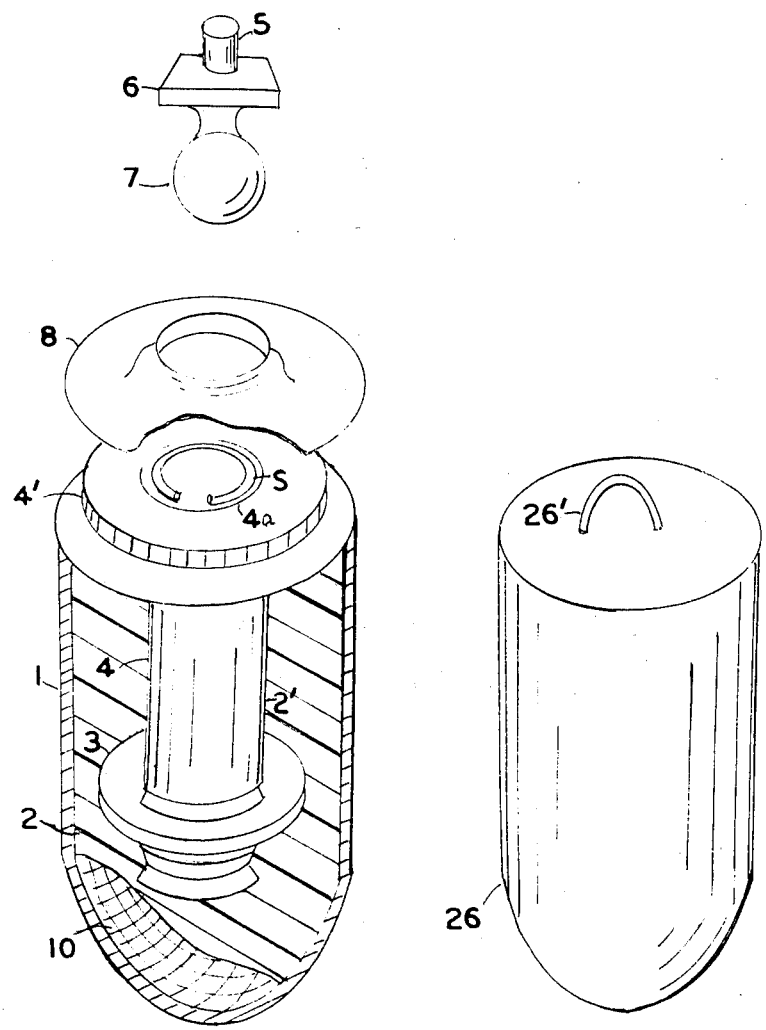
FIG 1
FIG 6
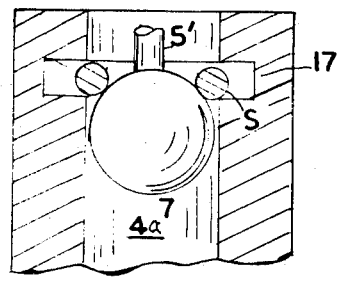
FIG 2

MASTICATION FORCE DAMPENING DENTAL JAWBONE IMPLANT

TECHNICAL FIELD

This invention relates to dental tooth replacement and more particularly to a mastication force dampening dental jawbone implant, and means and method for implanting the invention in the jawbone of a patient.

PRIOR ART

This invention is an improvement of U.S. Pat. No. 4,445,862, V. Chiaramonte and co-pending patent application, Ser. No. 638,199, filed Aug. 6, 1984, V. Chiaramonte.

U.S. Pat. No. 4,445,862 shows means for mounting a post between two good teeth by cutting grooves in the two good teeth.

Patent Application, Ser. No. 638,199, provides means for mounting a post between two good teeth by making implants in the two good teeth.

The conventional full upper and lower dentures depend upon friction and suction fits with adhesives and are subject to coming out easily when coughing, swimming, etc.

There is a need for improved denture mounting which do not affect or depend upon good teeth.

In order to understand oral implantology one should examine several basic concepts. An implant must be biocompatible. A material implanted in the body must be chemically and biologically inert to be acceptable to living tissue. An implant must also be biofunctional. It must be in configuration that takes maximum advantage of the bone available for implantation. A biocompatible material must not dictate configuration because of its adequate physical properties. An optimal configuration will enable maximum force transmission at the interface, fully utilizing the quantity of available bone within which it can be placed, all within physiologic limits of health. An optimal biocompatible material is then chosen for that configuration to ensure physical properties required for a successfully functioning implant. Any biocompatible material can be formed into some configuration that can be placed within a fixed amount of available bone, and project into the oral cavity through a pergingival site. If limited forces are placed on the implant, within physiologic limits of health, a normal clinical and histologic picture can be demonstrated. That is why one can demonstrate good histology around most implant configurations. What we seek is a configuration that will make a limited fixed amount of available bone most efficient, able to transmit the most force, and remain healthy. Such a configuration provides a better new implant abutment, with the greatest margin of safety in determining the prognosis of the planned prosthetic device. These implants may be utilized as all or part of the abutment system.

It is also important to understand the concept of available bone. Available bone is that bone into or onto which an implant may be placed. The amount and location of available bone is the key to differential diagnosis and treatment planning. It helps determine the type of implant that will be used, and type of prosthesis that will follow. The different groups of implants and implant modalities rarely compete with one another. Rather, the amount of available bone and ultimate support required of the implant dictate the modality to use in a specific case.

ENDOSSEOUS IMPLANTS—Those placed within the confines of residual edentulous alveolar ridges. Endosseous implants account for over 90% of the implants utilized. Endosseous blade implants account for over 85% of the group. They are the most ideal, providing the highest validated survival rate at this time. Other examples of endosseous implants are spirals, screws, baskets, staples, transosseous, various root forms, ramus frames, osteogenic bone pins and endodontic stabilizers. Some of these are accepted predictable modalities, others have been deemed not acceptable for patient use, and still others are so new that they have not yet been fully evaluated.

SUBPERIOSTEAL IMPLANTS—Those initially placed under the periosteium and mainly supported by key areas of basal bone. These represent approximately 5% of placed implants. They may be custom fabricated for the maxilla or the madible. There are three typs. For totally edentulous cases, the total subperiosteal implant is employed. For partially edentulous cases, the unilateral subperiosteal implant is chosen. When viable anterior teeth remain in an otherwise endentulous arch, the circumferential subperiosteal is utilized.

This implant would be classified as an Endosseous Implant but does not resemble any of the implants on the market today.

THE INVENTION

The present invention provides a new and improved dental jawbone implant wherein cylindrical casing is implanted in the jawbone. The casing has a resilient insert, for instance of rubber. The post for holding new teeth or a tooth is mounted on a threaded shaft which may be adjustably threaded into the resilient shock absorbing insert. The post is removably mounted by means of a spring holding means. Whereby, the present provides means for firmly mounting a tooth or denture directly on the jawbone without affecting or depending upon any good teeth thereby removing wear and tear and possible injury to the good tooth or teeth.

OBJECTS OF THE INVENTION

Accordingly, a principal object of the invention is to provide new and improved tooth and denture mounting means.

Another object of the invention is to provide new and improved tooth and denture mounting means which does not affect or depend upon good teeth.

Another object of the invention is to provide new and improved denture mounting means which does not depend upon friction or suction fits and adhesives.

Another object of the invention is to provide new and improved mastication force dampening dental implant means.

Another object of the invention is to provide new and improved mastication force dampening dental implant comprising: a cylindrical casing adapted to be implanted in a jawbone, a resilient insert in said casing, a first shaftway in said insert, a nut anchored in said insert coaxially with said first shaftway, a threaded shaft mounted in said first shaftway, the shaft being threaded into said nut, the shaft having a second shaftway in its top portion, a head fixedly connected to said first shaft at the top of the casing, a retention post mounted on said head, means to removably mount said retention post in the top of said second shaftway.

Another object of the invention is to supply a biocompatible dental implant that will be relatively inexpensive, whose exterior surface is coated with a material such as calcitite, manufactured by Calcitite, Inc., San Diego, California. Calcitite is a bone regenerating material and this coating on the outside of the implant will stimulate the growth of bone. Any other equally effective material could actually also be used. This implant will also have a shock absorber located internally and have a receptacle on its top so as to receive an artificial tooth.

BRIEF DESCRIPTION OF THE DRAWINGS

These and other objects of the invention will be apparent from the following specifications and drawings of which:

FIG. 1 is a front sectional view of an embodiment of the invention.

FIG. 2 is a detail view of the spring loaded retaining means.

FIGS. 4, 5 and 6, are perspective illustrative views.

BEST MODE OF THE INVENTION

Figure 3:
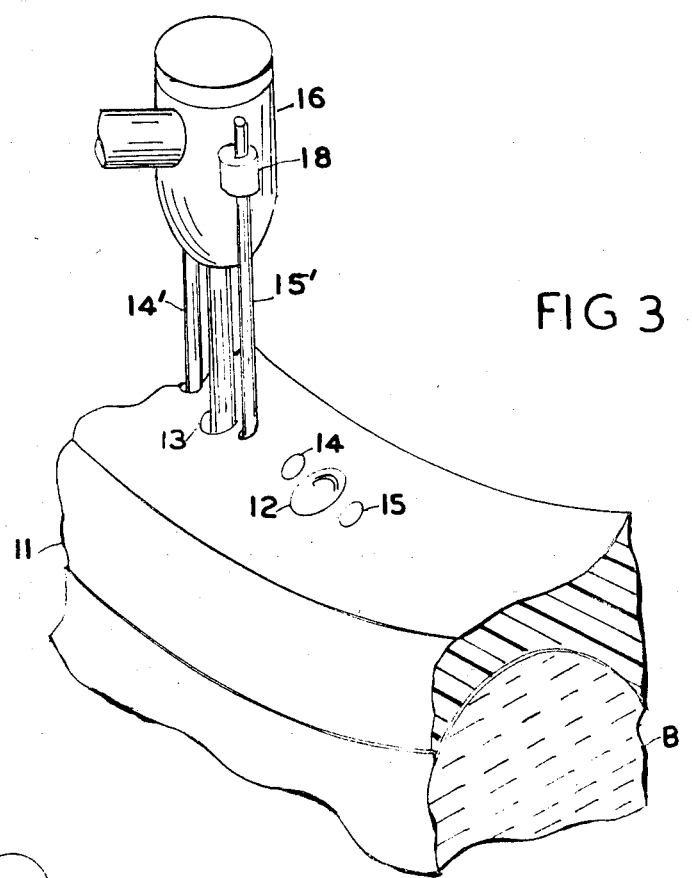
FIG. 3 is a perspective view of a template and drilling apparatus for inserting the implant of the present invention.

Referring to FIG. 1, the invention comprises a casing 1. A resilient insert 2 is mounted in the casing. The insert may be of rubber. The insert has a shaftway 2'. A nut 3 is anchored in the insert coaxially with the shaftway. A threaded shaft 4 is mounted in the shaftway and is threaded into the nut 3. The shaft 4 has a head 4' which is knurled around its outer edge. The shaft has a shaftway 4a in its upper portion.

The knurled retention post 5 for a tooth or denture is mounted on a base 6 which is connected to a ball 7, which fits into the shaftway 4a. The ball and post assembly preferably has a cover 8, which may be plastic, such as Nylon. The casing 1 may be of stainless steel or various plastics, such as Nylon, Delrin or equivalent. The casing 1 is preferably covered with a bone growth stimulating material such as hydroxyl apatite, which is coated on a mesh 10. This material has the property of increasing bone growth around the implant casing 1. The shaft 4 may be made of stainless steel or equivalent. The ball 7 and the retaining head 5 and its post 6 are preferably made of stainless steel.

FIGS. 2 and 2A show the spring means for holding the ball 7 in place for removably in the shaftway 4a. The spring S sits in the indentation 17 in the shaft 4 so that the ball 7 is held in place by the spring S. Therefore, the post 5 assembly, including the ball 7, can be easily snapped into place or removed as desired.

The mastication force dampening feature of the present invention permits movement of the new teeth similar to that of the natural teeth and promotes the good condition of the natural teeth which are abutting the new artificial teeth.

GENERAL PROCEDURE

Referring to FIG. 3 there is shown a template 11 which is made in conventional manner by the Dentist and Laboratory in the same manner as making an impression for a denture. The Dentist marks the holes 12 and 13 locations. The Dental Laboratory then makes the holes 12 and 13 and also guide holes 14 and 15.

The template is then returned to the Dentist who uses a conventional dental drill 16, modified in accordance with this invention, by the addition of two guide rods 14', 15'.

In drilling the holes for the implant the Dentist places the template 11 on the jawbone and its associated gum structure. The holes for the implants are then controlled by inserting the drill bit into the hole 12 and inserting the guide rods 14', 15', in the guide holes 14, 15.

THE DETAILED PROCEDURE IS AS FOLLOWS

1. An impression is taken by the dentist and sent to the Laboratory. A cast is made of the impression.

2. On that cast, selected artificial teeth are set up in wax so as to determine the proper location of the roots of the teeth.

3. A clutch or template 11 is constructed from the cast and this clutch or template is designed to record the root position of the teeth in a selected series of parallel drilled holes and related hole guides, FIG. 3. The purpose of these holes are to properly align the Dentist's drill when he is ready to cut the holes in the jawbone.

In FIG. 3, is a drawing of the drill 16. There are two parallel guide rods 14', 15', with retaining arms 18. The retaining arms guide the rods in place to guide the drill and drill bit precisely down and into the bone B. When the rods 14', 15', reach the jawbone the guide rods slide up in the retaining arms still guiding the drill.

4. With the clutch removed the stabilizing implants may be inserted.

Figure 4:
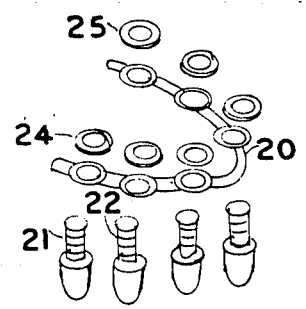

5. A stabilizing bar 20 is now constructed, FIG. 4. It is an onlay of wax or plastic around the implant screws 21, 22, etc. On each implant, a stabilizing nut 24, 25, is placed over the wax on the stabilizing bar squashing it slightly giving it a positive seat. It is then carefully removed from the stabilizing tables, sprued and invested, and through the lost wax technique, it is cast in stainless steel.

6. The clutch 11, and the stabilizing bar 20 are sent to the Dentist. The Dentist proceeds to surgically fold down the tissue and he then places the clutch and proceeds to carefully drill the bone using the specially designed drill. The holes should be slightly oversized. The tissue is then reattached.

Figure 5:
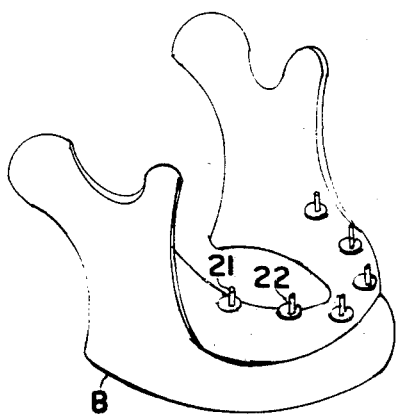

7. He then places the implants in the jawbone B., FIG. 5, then he places the stabilizing bar 20 over the implants and tightens the stabilizing lock nuts 24, 25, FIG. 4. A temporary denture was also made at the Laboratory and the Dentist places this over the implants and stabilizing bar. A period of four to eight weeks will be needed to form the new bone.

8. After the new bone is formed, the Dentist removes the temporary denture and stabilizing lock nuts 24, 25, FIG. 4, removes the stabilizing bar 20, loosens the rubber compressing shaft 4, FIG. 1, removes the entire shock absorbing mechanism. He does this on each implant.

9. Into each cylinder 1, the Dentist places a dummy transfer 26, FIG. 6, which fits snugly into the cylinder. The design of the dummy is such that it will be picked up in the impression material, by retention loop 26'.

10. The Dentist takes the impression with the dummies in place and removes it when it is set. The impression is carrying each of the dummies enfolded in it. He then sends it to the Laboratory along with the bite registration.

11. The Laboratory then places implant cylinders 1, over the dummies and pours a plaster model. When the model sets, the cast is separated from the impression and now in the cast the cylinders remain and it is now the negative. From this cast a finished denture can be made.

12. The Laboratory finishes the denture and sends it to the Dentist. The Dentist places the proper shock absorbing assembly into the implant cylinder(s) and simply snaps in the restoration.

It is claimed:

1. Mastication force dampening dental implant comprising:
   a cylindrical casing adapted to be implanted in a jawbone,
   a resilient insert in said casing,
   a first shaftway in said insert,
   a nut anchored in said insert coaxially with said first shaftway,
   a threaded shaft mounted in said first shaftway, the shaft being threaded into said nut,
   the shaft having a second shaftway in its top portion,
   a head fixedly connected to said first shaft at the top of the casing,
   a retention post mounted on said head,
   means to removably mount said retention post and head in the top of said second shaftway.

2. Apparatus as in claim 1 wherein the removable mounting means is a ball connected to the retention post and adapted to fit into the second shaftway, and spring means mounted in the second shaftway to hold the ball in place.

3. Apparatus as in claim 1 wherein the outside of the casing is covered with bone growth stimulating material.

4. Apparatus as in claim 3 wherein the bone growing material is calcitite coated mesh.

5. Apparatus as in claim 1 wherein the resilient insert is of rubber.

6. Dental implant comprising:
   a casing adapted to be implanted in a jawbone,
   a resilient insert in said casing,
   a shaftway in said insert,
   a threaded shaft mounted in said first shaftway, the shaft being threaded into said insert,
   and a retention post mounted on said shaft.

7. Process of implanting a dental implant in a jawbone of a patient comprising the steps of;
   making an impression of the jawbone,
   marking the location of at least one implant on the impression,
   making a template from the impression,
   drilling at least one hole in the template corresponding to said marking,
   placing the template on the jawbone,
   drilling implant holes through the holes in the template,
   placing an implant in each hole in the jawbone.

8. The process as in claim 7 where the step of drilling holes in the template includes drilling guide holes.

* * * * *